(12) United States Patent
Holland

(10) Patent No.: US 10,869,971 B2
(45) Date of Patent: Dec. 22, 2020

(54) SAFETY SYRINGE APPARATUS

(71) Applicant: Owen Mumford Ltd., Oxfordshire (GB)

(72) Inventor: Damian Alexander Holland, Oxfordshire (GB)

(73) Assignee: Owen Mumford Limited, Oxford (GB)

( * ) Notice: Subject to any disclaimer, the term of this patent is extended or adjusted under 35 U.S.C. 154(b) by 269 days.

(21) Appl. No.: 16/066,434

(22) PCT Filed: Jan. 19, 2017

(86) PCT No.: PCT/GB2017/050113
§ 371 (c)(1),
(2) Date: Jun. 27, 2018

(87) PCT Pub. No.: WO2017/125731
PCT Pub. Date: Jul. 27, 2017

(65) Prior Publication Data
US 2019/0001072 A1    Jan. 3, 2019

(30) Foreign Application Priority Data

Jan. 19, 2016 (GB) .................................. 1600989.6

(51) Int. Cl.
*A61M 5/32* (2006.01)
(52) U.S. Cl.
CPC .......... *A61M 5/326* (2013.01); *A61M 5/3213* (2013.01); *A61M 5/3245* (2013.01);
(Continued)

(58) Field of Classification Search
CPC .. A61M 5/322; A61M 5/3221; A61M 5/3243; A61M 5/3245; A61M 5/3257;
(Continued)

(56) References Cited

U.S. PATENT DOCUMENTS

| 5,163,917 A | 11/1992 | Huefner et al. |
| 5,562,626 A * | 10/1996 | Sanpietro ............. A61M 5/326 604/110 |

(Continued)

FOREIGN PATENT DOCUMENTS

| EP | 2 752 211 | 7/2014 |
| GB | 2529507 | 2/2016 |

(Continued)

OTHER PUBLICATIONS

IPO Search report Application No. GB1600989.6 dated, Jul. 11, 2016.

(Continued)

*Primary Examiner* — Kevin C Sirmons
*Assistant Examiner* — Tezita Z Watts
(74) *Attorney, Agent, or Firm* — Quarles & Brady LLP

(57) ABSTRACT

An apparatus for use with a syringe for providing a safety syringe, the apparatus including a sheath (100; 300; 500) deployable for at least partially covering a needle (126) of the syringe; and a sheath actuator (102; 302; 502) for deploying the sheath by interaction with a sheath deployment mechanism (104; 304; 504); the sheath being configured to be stationary in relation to the needle until a syringe plunger (116; 316; 516) reaches a sheath release point on its inward stroke, and the sheath actuator being configured for deployment of the sheath on movement of the sheath actuator relative to the syringe plunger after the sheath release point.

23 Claims, 5 Drawing Sheets

(52) U.S. Cl.
CPC ............... *A61M 2005/3247* (2013.01); *A61M 2005/3261* (2013.01)

(58) Field of Classification Search
CPC .. A61M 5/326; A61M 5/3232; A61M 5/3234; A61M 5/3276; A61M 5/3213; A61M 5/32; A61M 2005/3261; A61M 2039/042; A61M 2005/3226; A61M 2005/3237; A61M 2005/3247; A61M 2005/325; A61M 2005/3258; A61M 2005/3264
See application file for complete search history.

(56) References Cited

U.S. PATENT DOCUMENTS

| | | | |
|---|---|---|---|
| 6,186,980 B1* | 2/2001 | Brunel | A61M 5/3202 604/110 |
| 6,623,459 B1 | 9/2003 | Doyle | |
| 7,429,256 B2 | 9/2008 | Chevallier et al. | |
| 7,963,949 B2 | 6/2011 | Chevallier et al. | |
| 8,231,571 B2 | 7/2012 | Chevallier et al. | |
| 8,235,967 B2 | 8/2012 | Chevallier et al. | |
| 8,617,105 B2 | 12/2013 | Chevallier et al. | |
| 8,979,794 B2 | 3/2015 | Chevallier et al. | |
| 9,446,204 B2 | 9/2016 | Teucher et al. | |
| 2002/0156426 A1 | 10/2002 | Gagnieux | |
| 2002/0193746 A1 | 12/2002 | Chevallier et al. | |
| 2003/0149403 A1* | 8/2003 | Barker | A61B 5/150732 604/198 |
| 2005/0277894 A1 | 12/2005 | Westbye et al. | |
| 2008/0312603 A1 | 12/2008 | Chevallier et al. | |
| 2011/0213313 A1 | 9/2011 | Chevallier et al. | |
| 2011/0213334 A1 | 9/2011 | Chevallier et al. | |
| 2012/0271276 A1 | 10/2012 | Chevallier et al. | |
| 2013/0289490 A1* | 10/2013 | Kemp | A61M 5/3287 604/198 |
| 2014/0081213 A1 | 3/2014 | Chevallier et al. | |
| 2014/0194828 A1 | 7/2014 | Teucher et al. | |
| 2015/0182704 A1 | 7/2015 | Chevallier et al. | |

FOREIGN PATENT DOCUMENTS

| | | |
|---|---|---|
| WO | WO 01/41841 | 6/2001 |
| WO | WO 2004/043524 | 5/2004 |

OTHER PUBLICATIONS

International Search Report, PCT/GB2017/050113, dated Apr. 24, 2017.
Written Opinion, PCT/GB2017/050113, dated Apr. 24, 2017.

* cited by examiner

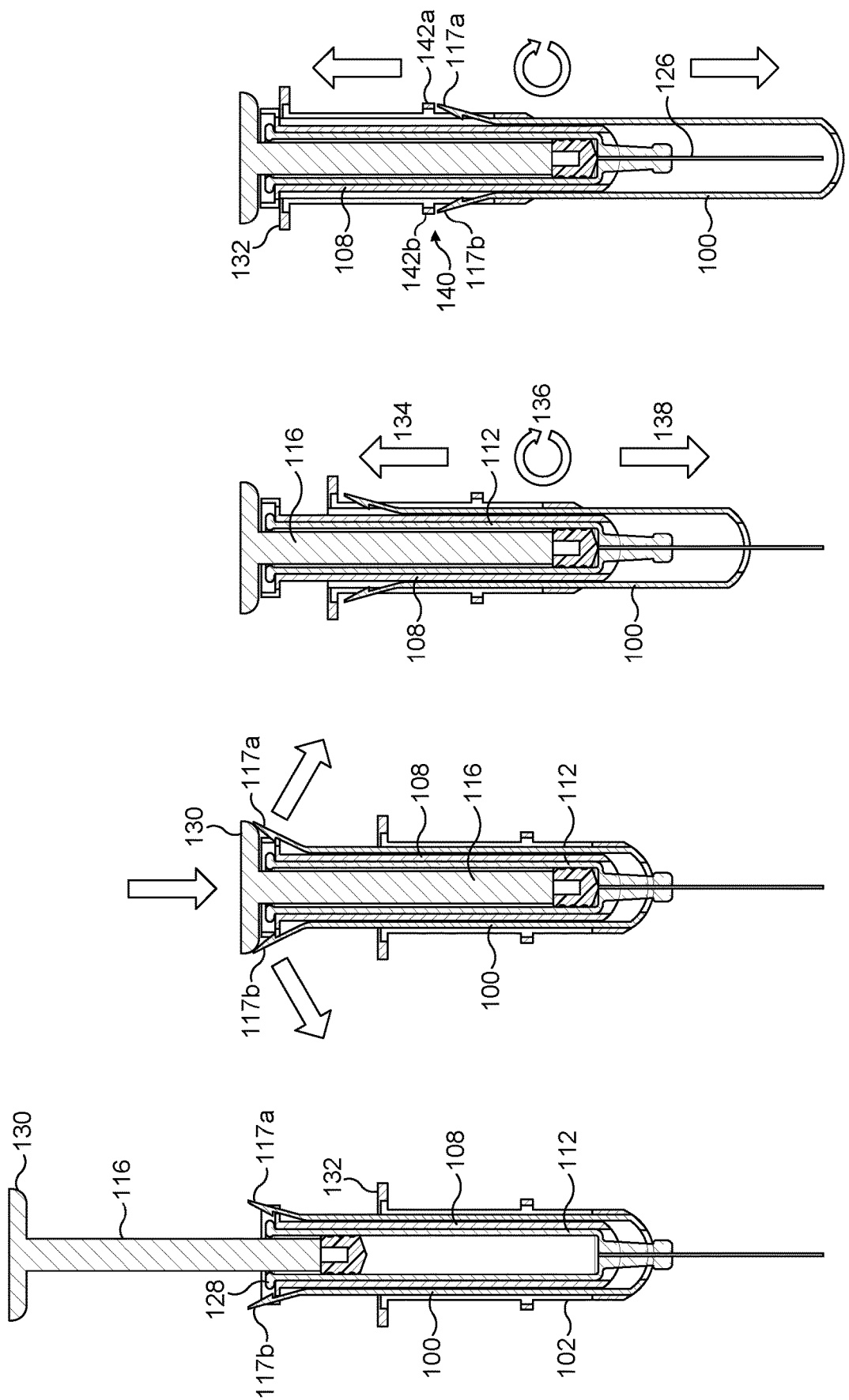

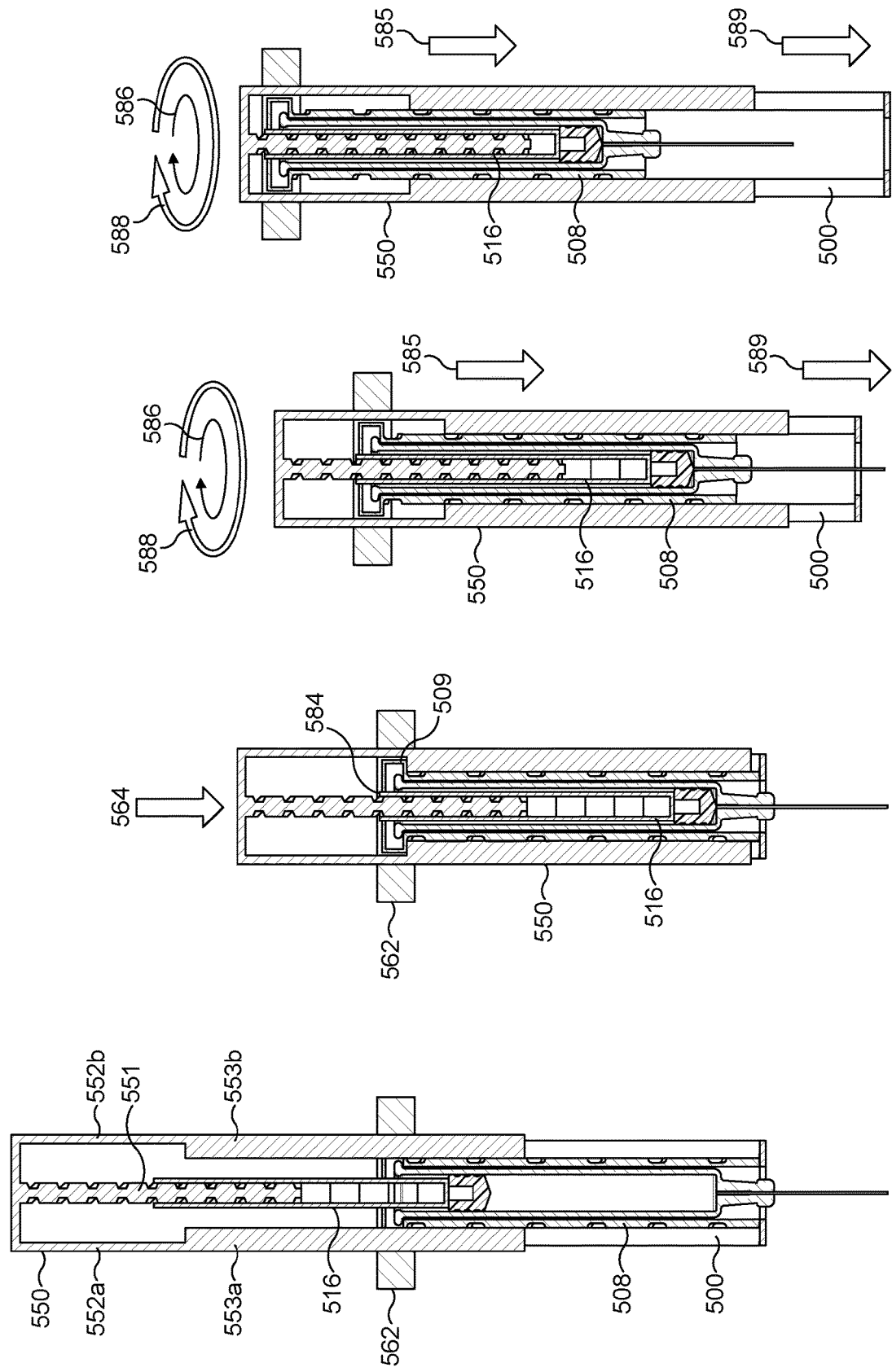

SAFETY SYRINGE APPARATUS

TECHNICAL FIELD

The invention relates to safety syringes and apparatus for fitting to syringes to convert them to safety syringes. In particular embodiments, the invention relates to, but need not be limited to, passive safety syringes and associated apparatus.

BACKGROUND

Broadly, syringes for medical use comprise a barrel having a hypodermic needle at one end and a plunger configured to move within the barrel such that an inward stroke of the plunger causes a substance contained within the barrel to be expelled from an aperture in the needle.

Safety syringes typically include some form of safety mechanism to protect healthcare workers from the hypodermic needle after it has been injected into a patient. Exemplary safety syringes may include a sheath for covering the needle, or may cause the needle to retract within the barrel of the syringe.

Safety syringes may be broadly split into 'active' and 'passive'. Active safety syringes typically require some action by a user of the syringe to engage the safety mechanism. Such action may be taken after removal of the needle from the patient, or may be taken during removal of the needle from the patient. Typically, the action required to engage the safety mechanism is separate from the action required to cause the inward stroke of the plunger. Passive safety syringes typically engage the safety mechanism without any specific action by the user, that is, without any action other than that usually taken to use the syringe.

SUMMARY

The inventors have appreciated that a safety syringe may comprise a spring-loaded safety mechanism that may be engaged by a healthcare worker after, and separate to, the inward stroke of the plunger. That is, the healthcare worker takes a separate action to engage the spring-loaded mechanism. The spring force urges a surface against the skin of the patient, thereby extracting the needle and simultaneously engaging a safety mechanism, such as a sheath. Such devices are prone to misuse as healthcare workers are known to remove the needle from the patient before engaging the safety mechanism. This exposes the healthcare worker to the needle after use and the spring-loaded action of the safety mechanism may lead to blood splatter from the needle.

Other known safety syringes require the needle to be removed from the patient before the safety mechanism may be engaged. This exposes the healthcare worker to the needle after use.

According to an aspect of the invention, there is provided an apparatus for use with a syringe for providing a safety syringe, the apparatus comprising: a sheath deployable for at least partially covering a needle of the syringe; and a sheath actuator for deploying the sheath by interaction with a sheath deployment mechanism; wherein the sheath is configured to be stationary in relation to the needle until a syringe plunger reaches a sheath release point on its inward stroke, and wherein the sheath actuator is configured for deployment of the sheath on movement of the sheath actuator relative to the syringe plunger after the sheath release point.

Optionally, the sheath actuator is configured to be operated by a continued syringe operation action by a user after the sheath release point.

Optionally, the sheath actuator is configured to move relative to the syringe plunger under a force applied by the user during the continued syringe operation action.

Optionally, movement of the sheath actuator relative to the syringe plunger after the sheath release point causes operation of the sheath deployment mechanism, and wherein there is a continuous relationship between movement of the sheath actuator relative to the syringe plunger after the sheath release point and movement of the sheath.

Optionally, the sheath actuator is slidably mountable to the syringe.

Optionally, the sheath deployment mechanism comprises a pinion for interaction with a first rack on the sheath actuator and a second rack on the sheath.

Optionally, the apparatus further comprises a mount, fixed in relation to the syringe and on which the pinion is mounted.

Optionally, the sheath deployment mechanism comprises a rotatable linkage comprising a first thread configured to translate rotation of the linkage into linear motion of the sheath for deployment thereof.

Optionally, the sheath actuator is configured to rotate the rotatable linkage on movement of the sheath actuator after the sheath release point.

Optionally, the sheath deployment mechanism comprises a second thread, opposed to the first thread and configured to interact with the sheath actuator for rotation of the rotatable linkage.

Optionally, the second thread is located on the rotatable linkage.

Optionally, the sheath actuator is configured to be fixed in relation to the syringe until the syringe reaches the sheath release point.

Optionally, the sheath actuator comprises a handle portion for receiving a user's index and middle fingers during a syringe operation action.

Optionally, the sheath comprises retaining lugs for holding the sheath stationary with respect to the needle, and configured to be released when the syringe plunger reaches the sheath release point.

Optionally, the sheath, sheath deployment mechanism and sheath actuator are connected such that release of the retaining lugs allows movement of the sheath actuator and operation of the sheath deployment mechanism.

Optionally, the sheath actuator comprises a safety plunger for linear coupling to the syringe plunger and configured to decouple from the syringe plunger at the sheath release point.

Optionally, the sheath deployment mechanism comprises a threaded rod extending from the safety plunger, wherein the second thread is located on threaded rod and is configured to rotate the linkage on a continued syringe operation action by the user after the sheath release point.

Optionally, the apparatus further comprises the syringe plunger, wherein the threaded rod is configured to be received in a corresponding recess of the syringe plunger for rotation thereof, and wherein the syringe plunger is rotationally coupled to the linkage.

Optionally, the apparatus further comprises a rotation restrictor configured to prevent rotation of the syringe plunger until after the sheath release point.

Optionally, the rotation restrictor comprises features of one or more legs of the safety plunger configured to interact with corresponding features of the linkage for preventing rotation thereof.

Optionally, the features of the one or more legs of the safety plunger comprise a rib, and wherein the corresponding feature of the linkage comprises a slot configured to receive the rib.

Optionally, the rotation restrictor comprises a keyed guide configured to interact with the syringe plunger to prevent rotation thereof.

Optionally, the keyed guide comprises a keyed aperture through which the syringe plunger passes, wherein at least part of the syringe plunger has a cross section configured not to be rotatable within the keyed aperture.

According to the invention in another aspect, there is provided a safety syringe comprising an apparatus according to any preceding claim.

According to the invention in another aspect, there is provided a kit of parts for use with a syringe for providing a safety syringe, the kit of parts comprising: a sheath deployable for at least partially covering a needle of the syringe; a sheath deployment mechanism; and a sheath actuator for deploying the sheath by interaction with the sheath deployment mechanism; wherein the sheath is configured, when fitted to a syringe, to be stationary in relation to the needle until a syringe plunger reaches a sheath release point on its inward stroke, and wherein the sheath actuator is configured for deployment of the sheath on movement of the sheath actuator after the sheath release point.

Optionally, the kit of parts further comprises a syringe to which the sheath, sheath deployment mechanism and sheath actuator are configured to be fitted.

Optionally, the syringe is prefilled with a medicament.

BRIEF DESCRIPTION OF DRAWINGS

FIGS. 2a-d show stages of operation of an exemplary apparatus fitted to a syringe for providing a safety syringe;

FIGS. 6a-d show stages of operation of an exemplary apparatus fitted to a syringe for providing a safety syringe.

DETAILED DESCRIPTION

Figure 1:
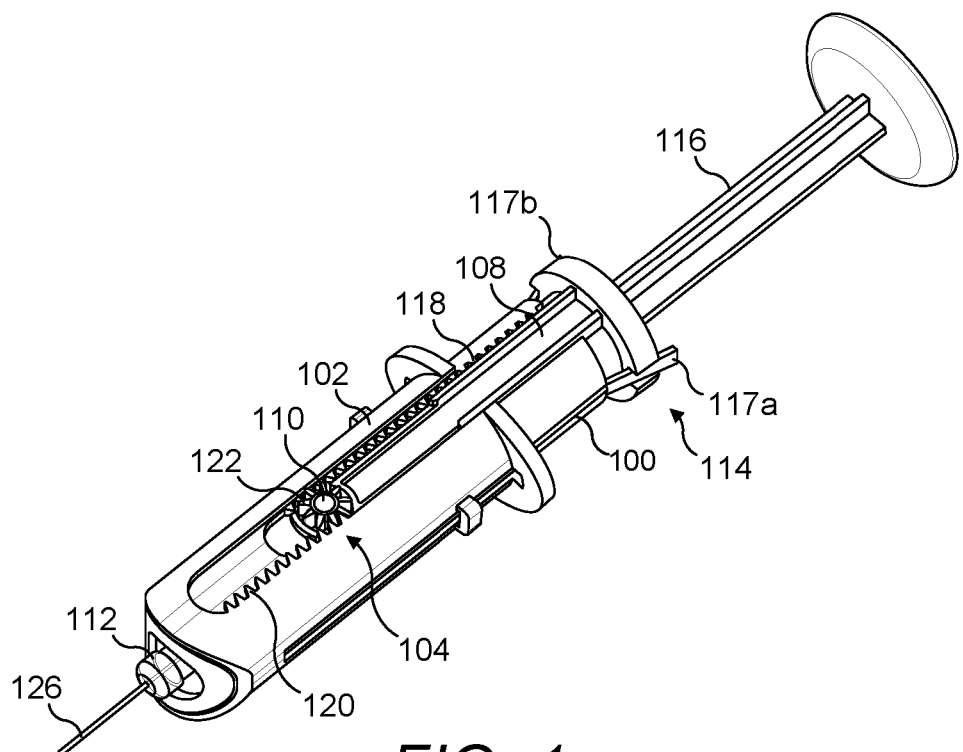
FIG. 1 is a perspective view of an exemplary apparatus fitted to a syringe.

Generally, disclosed herein are safety syringes and apparatus for providing safety syringes, in which a sheath is deployed by a mechanism actuated by a sheath actuator. In exemplary apparatus, the sheath is extended along a length of a barrel of a syringe to cover at least partially a needle of the syringe. The sheath may be urged over the needle by a force applied by the user, typically during a syringe operation action, which involves action for normal use of the syringe. In exemplary apparatus, a force applied by the user after a sheath release point may move the sheath actuator relative to a syringe plunger and that relative movement is translated into a corresponding movement of the sheath. Accordingly, there is a continuous relationship between the relative movement of the sheath actuator and the syringe plunger and the movement of the sheath. This is distinct from an apparatus in which a sheath is deployed by release of a self-operating mechanism, e.g. by a biasing member.

A sheath actuator interacts with a sheath deployment mechanism to deploy the sheath. In some arrangements, the movement of the sheath is ratioed with respect to movement of the sheath actuator such that a magnitude of movement of the sheath is greater than a magnitude of movement of the sheath actuator. The ratioed movement may be provided by the sheath deployment mechanism.

Further, the sheath actuator may be configured to cause deployment of the sheath from in-line movement thereof. The term "in-line" is used to encompass longitudinal movement aligned with a longitudinal axis of the safety syringe. In-line movement may be caused by a syringe operation action of a user using a syringe. In exemplary apparatus, a syringe operation action encompasses the depression of a plunger by a thumb while retaining the syringe barrel using the index and middle fingers of the same hand. The syringe operation action may be continued after a full stroke of a syringe plunger moving within the barrel for expulsion of a substance from the barrel.

It is noted that, although the apparatus described relate to syringes including a barrel, needle and syringe plunger, exemplary apparatus may also relate to an apparatus for fitting to a syringe. That is, exemplary apparatus need not include the barrel, needle and/or syringe plunger.

As used herein, the term "syringe plunger" encompasses a plunger that has an element configured to move within a barrel of a syringe to dispense a substance contained within the barrel.

Further, exemplary apparatus are described herein and relate to relative movement between various features of the apparatus. It should be understood that it is relative movement that is used to operate some of the features of the apparatus. For example, a sheath actuator may be moved and the syringe remain stationary in order to deploy a sheath, but the same effect may be achieved by movement of a syringe if the sheath actuator remains stationary. The descriptions provided herein assume that the syringe remains stationary.

FIG. 1 shows an exemplary apparatus for fitting to a syringe for providing a safety syringe. The apparatus is shown fitted to a syringe in FIG. 1. The apparatus comprises a sheath 100 and a sheath actuator 102. A sheath deployment mechanism 104 links the sheath 100 and the sheath actuator 102 such that movement of the sheath actuator 102 causes movement of the sheath 100. In the exemplary apparatus of FIG. 1, the sheath deployment mechanism 104 comprises a rack and pinion arrangement. The sheath deployment mechanism 104 of the exemplary apparatus of FIG. 1 is configured to cause movement of the sheath 100 in an opposite direction to the movement of the sheath actuator 102. Further, the sheath deployment mechanism 104 may be configured such that the movement of the sheath 100 is greater than the corresponding movement of the sheath actuator 102.

The sheath deployment mechanism 104 comprises a mount 108, to which a pinion 110 is rotatably connected. The mount 108 is fixed to a barrel 112 of the syringe when the apparatus is fitted to the syringe. The sheath 100 and the sheath actuator 102 are configured to be slidable relative to the mount 108. Specifically in the exemplary apparatus of FIG. 1, the sheath 100 is arranged to slide on an outer surface of the mount 108 and the sheath actuator 102 is configured to slide on an outer surface of the sheath 100. The sheath 100 has a fixing 114 comprising retaining lugs 117a, 117b that is configured to hold the sheath 100 in fixed relation to the mount 108 (and/or the barrel 112) until such time as it is released at a sheath release point on the stroke of a syringe plunger 116. This is explained in greater detail below. The stroke of the syringe plunger 116 encompasses the inward and/or outward movement of the syringe plunger 116 within the syringe barrel 112. The fixing 114 comprise two retaining lugs 117a, 117b configured to engage with a lip (shown in FIGS. 2a-d) at a syringe plunger opening of the barrel 112 or with a lip of the mount 108.

The exemplary apparatus of FIG. 1 prevents movement of the sheath actuator 102 because the sheath 100 is fixed in relation to the barrel 112 until the syringe plunger 116 reaches the sheath release point. As a result of the linkage between the sheath 100 and the sheath actuator 102 provided by the sheath deployment mechanism 104, none of those features is operable until the sheath fixings 114 are released.

The sheath deployment mechanism 104 further comprises a first rack 118 formed on the sheath 100 and a second rack 120 formed on the sheath actuator 102. The first and second racks 118, 120 are engaged with the pinion 110. In exemplary arrangements, the pinion 110 comprises a set of teeth 122 engaged with the first and second racks 118, 120. This provides a one-to-one motion of the sheath 100 to the sheath actuator 102. In other exemplary arrangements, there may be first and second sets of teeth on the pinion and the second set of teeth may have a greater radius than the first set of teeth, such that movement of the sheath actuator 102 causes a greater or lesser magnitude of movement of the sheath 100. However, the diameter of the first and second racks may be the same. In the exemplary arrangement of FIG. 1, the first and second racks 118, 120 each be engaged with a single set of teeth 122 of the pinion 110 such that movement of the sheath 100 is on a one-to-one ratio with movement of the sheath actuator 102.

The sheath 100 is extendable over at least part of the length of the apparatus such that it covers a needle 126 of the syringe after use thereof.

FIGS. 2a-d show a section through the apparatus and syringe of FIG. 1 at various stages of the operation.

Referring to FIG. 2a, the apparatus is in an unused condition. The mount 108 is fitted to the lip 128 at the syringe plunger aperture of the barrel 112. The lugs 117a-b of the fixing 114 are engaged with a lip of the mount 108, such that the sheath 100 is in a fixed relation to the mount 108 and the barrel 112. The syringe plunger 116 is at an outermost point on its stroke.

A user depresses the syringe plunger 116, which may be done by placing the thumb on a syringe plunger head 130 and the index and middle fingers against a finger grip 132 of the sheath actuator 102 and applying a relative pressure between the thumb and fingers. This concept of operation is typical in syringes. Because the sheath 100 is fixed in relation to the mount 108 and barrel 112, the sheath actuator 102 is prevented from moving, as it is linked to the sheath 100 by the sheath deployment mechanism 104 (not shown in FIGS. 2a-d, as they are sections). The second rack 120 is prevented from rotating the pinion 110 because the first rack 118 is fixed.

Referring to FIG. 2b, when the syringe plunger 116 reaches a sheath release point on its inward stroke (the end of the inward stroke in the exemplary apparatus of FIGS. 1 & 2a-d), the syringe plunger head 130 meets the retaining lugs 117a-b and displaces them laterally out of engagement with the lip of the mount 108. The fixing 114 is therefore released and the sheath 100 is no longer in fixed relation to the mount 108 and/or barrel 112. As such, the sheath actuator 102 is now free to move and to interact with the sheath deployment mechanism 104. It is noted that other forms of decoupling of the sheath actuator 102 are possible. Exemplary decoupling means are configured to retain the sheath actuator 102 in position until the plunger reaches the sheath release point on the inward stroke.

Referring to FIG. 2c, movement of the syringe plunger 116 after the sheath release point results in movement of the sheath actuator 102 relative to the mount 108 and/or the barrel 112. Movement of the sheath actuator 102 is represented by arrow 134. The sheath actuator interacts with the sheath deployment mechanism 104 and causes rotation of the pinion 110, which is represented by arrow 136. This in turn causes movement of the sheath 100, which is represented by arrow 138. The sheath 100 is thereby deployed towards its position at least partially covering the needle 126.

Referring to FIG. 2d, the sheath actuator 102 has moved to a limit of movement, at which the finger grip 132 abuts the lip of the mount 108. The sheath 100 is deployed, such that it covers the needle 126. Further, a lock 140 is engaged, such that the sheath may not be moved out of its extended position. The lock 140 of the exemplary apparatus of FIGS. 1 and 2a-d locks the sheath 100 in relation to the sheath actuator 102. Specifically, the lugs 117a-b are biased outwardly and therefore extend through apertures in the sheath actuator 102 such that they are restrained by locking surfaces 142a-b on the sheath actuator 102.

Figure 3:
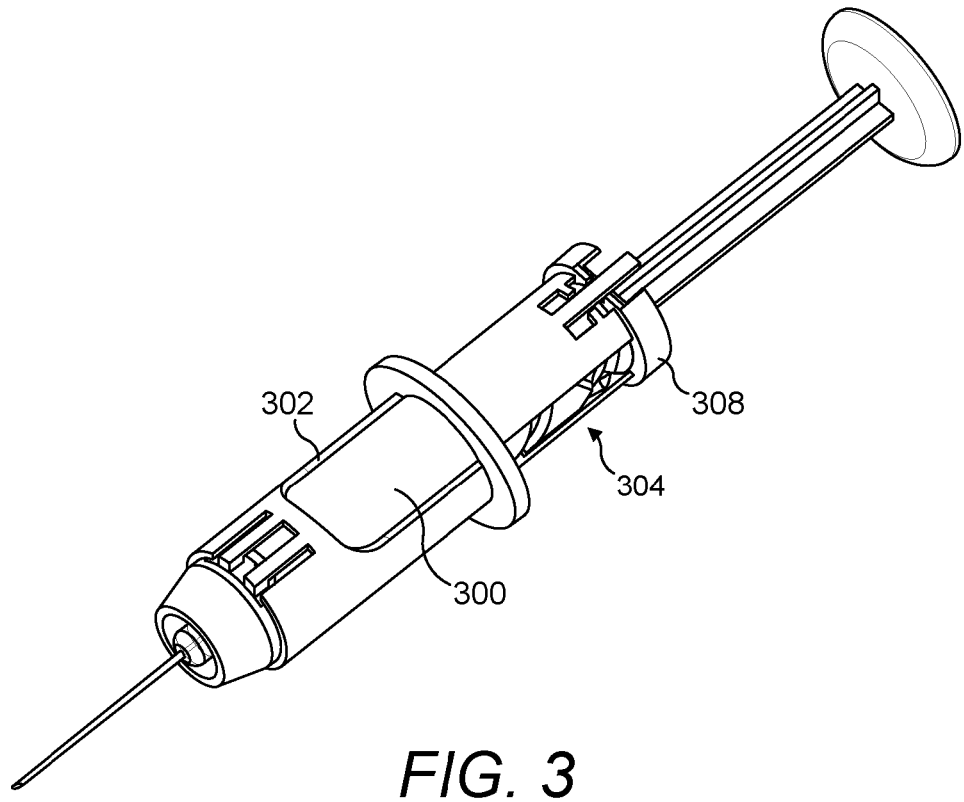
FIG. 3 is a perspective view of an exemplary apparatus fitted to a syringe.

FIG. 3 shows an exemplary apparatus fitted to a syringe. Many of the features of the apparatus of FIG. 3 are the same or similar to corresponding features of the apparatus of FIG. 1 and may have the same or a similar purpose. As such, these features are not described again in detail here. Similar reference numerals may be used for similar features, except prefixed by a "3".

A sheath deployment mechanism 304 of the exemplary apparatus of FIG. 3 comprises a rotatable linkage 308 that is rotatable relative to one or more of the barrel 312 (not shown in FIG. 3) of the syringe, the sheath 300 and the sheath actuator 302. The rotatable linkage 308 comprises a first thread 322 and a second thread 324, which are best shown in FIGS. 4a-d. The first thread 322 is configured to translate rotational movement of the linkage 308 into linear motion of the sheath 300. In the exemplary apparatus of FIG. 3, this is done by interaction with a corresponding feature on the sheath 300. The second thread 324 is configured to convert linear motion of the sheath actuator 302 into rotational motion of the linkage 308. In the exemplary apparatus of FIG. 3, this is done by interaction with corresponding features on the sheath actuator 302. In the exemplary apparatus of FIG. 3, the first and second threads 322, 324 comprise channels formed in the mount 308 and the corresponding features of the sheath 300 and the sheath actuator 302 comprise guiding lugs configured to travel within the channels.

It is noted that other arrangements for rotation of the linkage 308 are possible and need not be by way of a second thread.

The first and second threads 322, 324 need not form a full 360 degree revolution around the apparatus and may form a partial revolution. In this sense, first and second threads 322, 324 need not be a full helix (i.e. greater than a 360 degree revolution), but may be a curved guide formed around an outer of the linkage 308. The first and second threads 322, 324 are angled such that the sheath 300 and sheath actuator 302 respectively move along a length of the apparatus as the guiding lugs travel in the channels. The angle of the first and second threads 322, 324 refers to the steepness of the gradient of the threads, which controls the amount of linear motion translated by the guiding lugs from a given amount of rotational motion. In exemplary apparatus, the angle of each of the first and second threads 322, 324 is the same such that a one-to-one ratio of movement of the sheath 300 and sheath actuator 302 is provided. In other exemplary apparatus, the gradient of each thread may be different. The first and second threads 322, 324 are in opposed directions, such that movement of the sheath actuator 302 in one direction results in movement of the sheath 300 in an opposite direction.

FIGS. 4a-d show a number of side views of the exemplary apparatus of FIG. 3 at various stages of operation. The rotatable linkage 308 is rotatable with respect to the sheath 300 and the sheath actuator 302. As such, the linkage 308 may be rotatably connected to the barrel 312. The sheath 300 is connected to the linkage 308 by a fixing 314 comprising retaining lugs 317a-b. The first and second threads 322, 324 can be seen to be channels formed in the rotatable linkage 308. The sheath actuator 302 and the sheath 300 are not rotatable with respect to each other. The linkage 308 is configured to be rotatable with respect to the sheath 300 and the sheath actuator 302.

A user begins to operate the syringe by applying relative force between the finger grip 332 and the head 330 of the syringe plunger 316 to bring them together, similar to the process described in relation to FIGS. 2a-d. Because the sheath 300 is in a fixed relationship with the linkage 308, the linkage 308 cannot rotate and so guiding lugs of the sheath actuator 302 cannot travel in the second thread 324.

Figures 4A, 4B, 4C, 4D:
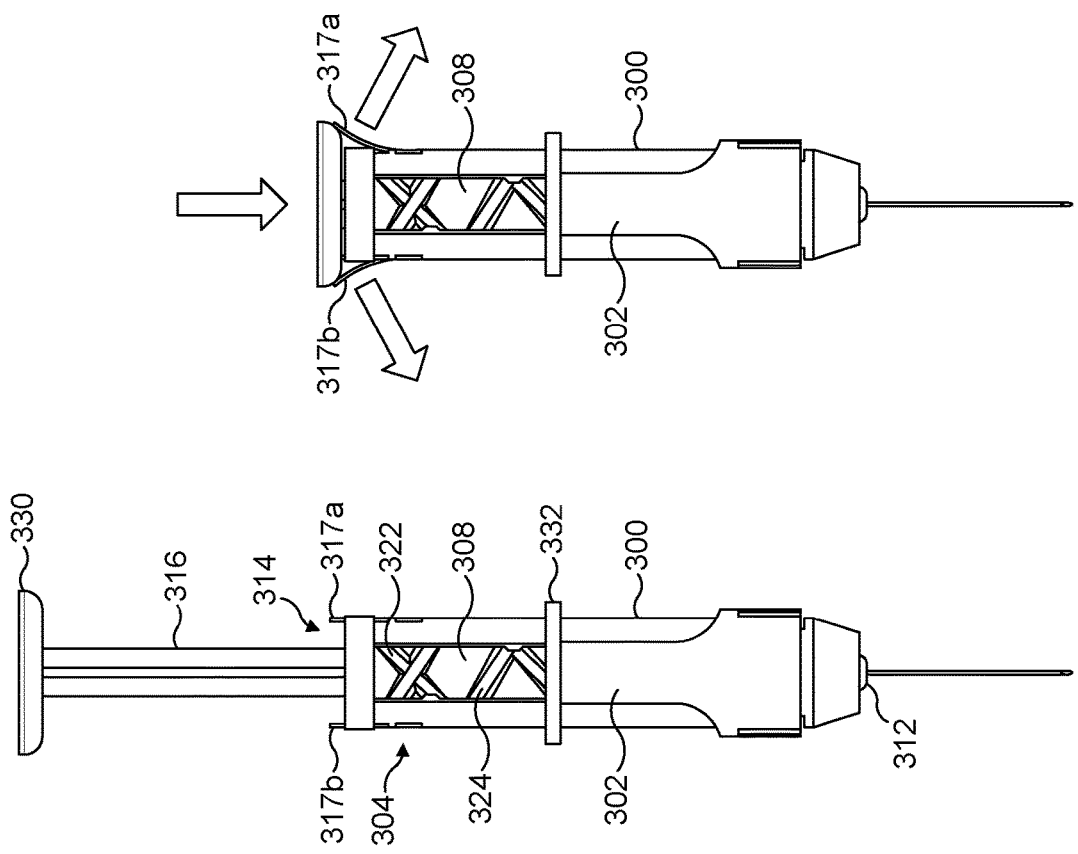
FIGS. 4a-d show stages of operation of an exemplary apparatus fitted to a syringe for providing a safety syringe.

Referring to FIG. 4b, when the syringe plunger 316 has reached the sheath release point, which may be the end of its stroke, the syringe plunger head 330 contacts the retaining lugs 317a-b and displaces them laterally such that they are no longer engaged with the linkage 308. The linkage 308 is now free to rotate with respect to the sheath 300 and the sheath actuator 302. As noted above in respect of FIG. 1, other forms of decoupling of the sheath 300 and/or sheath actuator 302 are possible. Generally, exemplary decoupling means are configured to retain the sheath 300 in position until the plunger reaches the sheath release point. After the sheath release point, the sheath actuator 302 is moveable to deploy the sheath 300.

As shown in FIG. 4c, movement of the sheath actuator 302 relative to the syringe plunger 316 (shown by arrow 334) after decoupling results in the guiding lugs of the sheath actuator 302 travelling within the second thread 324 in the direction shown by arrow 334, which in turn rotates the linkage 308 (shown by arrow 336) and forces the sheath 300 to move in the opposite direction (shown by arrow 338) because of the interaction of the guiding lugs on the sheath 300 and the first thread 322. FIG. 4d shows the sheath 300 fully deployed.

Figure 5A:
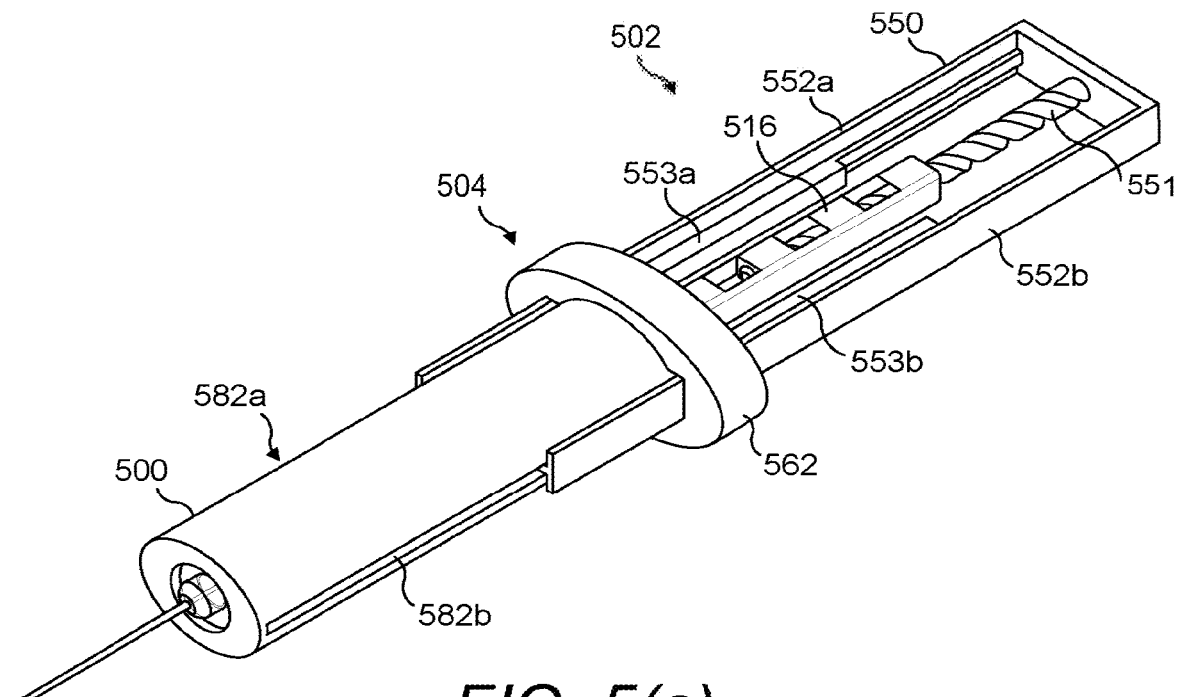
FIGS. 5a and 5b are perspective views of an exemplary apparatus fitted to a syringe.
Figure 5B:
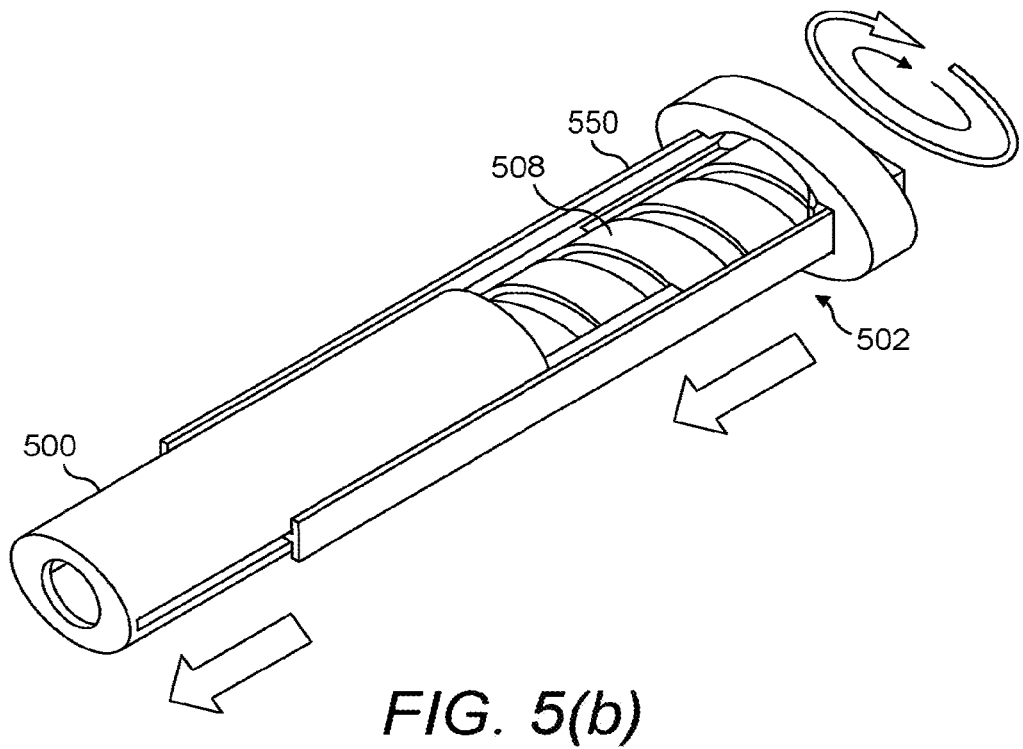

FIGS. 5a and 5b show an exemplary apparatus fitted to a syringe for providing a safety syringe. FIG. 5a shows the apparatus before use and FIG. 5b shows the apparatus during use at a point in which a rotatable linkage is visible. Some of the features of the apparatus of FIGS. 5a and 5b are the same or similar to corresponding features of the apparatus of FIGS. 1 and 3 and may have the same or a similar purpose. As such, these features are not described again in detail here. Similar reference numerals may be used for similar or the same features, except prefixed by a "5".

The exemplary apparatus of FIGS. 5a and 5b comprises a sheath 500 and a sheath actuator 502. The sheath actuator 502 comprises a safety plunger 550 that is coupled to a syringe plunger 516 and configured to decouple from the syringe plunger 516 at a sheath release point on the inward stroke. There are a number of ways that such decoupling may occur and one way is described below. After decoupling, further movement of the safety plunger 550 causes deployment of the sheath 500.

As used herein, the term "safety plunger" encompasses a feature of exemplary apparatus that is configured to deploy a sheath. Safety plungers may deploy the sheath on a normal syringe operating action of the user, that is, the user may operate the apparatus as normal and the syringe plunger will deploy the sheath under the applied force.

The sheath deployment mechanism 504 of the exemplary apparatus of FIGS. 5a and 5b also comprises a rotatable linkage 508 comprising a first thread and providing a threaded linkage between the sheath 500 and the sheath actuator 502. The linkage 508 is visible in FIG. 5b. The linkage 508 is configured to act as a lead screw for translating rotary motion of the linkage 508 into linear motion of the sheath 500, as explained below. The linkage 508 cooperates with corresponding features, for example a corresponding thread, of the sheath 500 to translate rotational motion of the linkage 508 into linear motion of the sheath 500. Specifically, the linkage 508 comprises a first thread configured to interact with corresponding features on the sheath 500.

The safety plunger 550 comprises a head and a plurality (two in the exemplary apparatus of FIG. 5) of legs 552a, b extending towards the sheath 500. The sheath 500 comprises guide channels 582a, b into which a corresponding feature of the legs 552a, b are received. The guide channels 582a, b allow relative linear movement of the sheath 500 and the legs 552a, b.

The safety plunger 550 is coupled to the syringe plunger 516 at a start point of the stroke. The safety plunger 550 is linearly coupled to the syringe plunger 516 in that linear movement of the safety plunger 550 results in linear movement of the syringe plunger 516. In the exemplary apparatus of FIGS. 5a and 5b, the coupling is provided by interaction between the legs 552a, b of the safety plunger 550 and corresponding features on the linkage 508. A threaded rod 551 of the safety plunger 550 comprises a second thread that exerts a rotational force on the syringe plunger 516, but the syringe plunger 516 is prevented from rotating along at least part of its stroke by the interaction between the legs 552a, b of the safety plunger 550 and corresponding features on the linkage 508 such that linear coupling is provided. The apparatus further comprises a rotation restrictor configured to prevent rotation of the linkage until the sheath release point. The rotation restrictor may comprise the legs 552a, b and the linkage 508, which may be configured to prevent rotation of the linkage 508 until the sheath release point on the inward stroke of the safety plunger 550. This in turn provides linear coupling between the safety plunger 550 and the syringe plunger 516 because the syringe plunger 516 is rotationally coupled to the linkage 508 and so is not free to rotate. In the exemplary apparatus of FIGS. 5a and 5b, ribs 553a, b on the legs 552a, b are configured to be received in slots in a lip 509 (shown in FIG. 6b) of the linkage 508 to prevent rotation of the linkage 508. The ribs 553a, b do not extend along the entire length of the legs 552a, b and an upper portion of each leg 552a, b has no rib 553a, b. Therefore, once the ribs 553a, b have passed through the slots, the linkage 508 is free to rotate and the syringe plunger 516 is no longer linearly coupled to the safety plunger 550. Continued movement of the safety plunger 550 therefore causes the threaded rod 551 of the safety plunger 550 to rotate the syringe plunger 516, which is rotationally coupled to the linkage 508, which therefore also rotates.

In alternative arrangements, the rotation restrictor may be provided by a combination of the threaded rod 551 extending from a head of the safety plunger 550 a keyed guide at entry of the syringe plunger 516 into the barrel of the syringe. The threaded rod 551 comprises a second thread that is received within the syringe plunger 516 and exerts a rotational force thereon. However, the syringe plunger 516 has a cross section along at least part of its length that prevents it from rotating due to interaction with the keyed guide. Rotation of the syringe plunger 516 is prevented by a non-circular cross sectional shape of the syringe plunger 516 interacting with a corresponding aperture at the entrance to the barrel. The syringe plunger 516 is configured to be rotatable at a point on the stroke, such that the safety plunger 550 and the syringe plunger become linearly decoupled, that is, linear motion of the safety plunger 550 need not result in linear motion of the syringe plunger 516. In the exemplary apparatus of FIG. 5, linear decoupling occurs when the syringe plunger 516 passes completely through the keyed aperture. This occurs at the sheath release point and the syringe plunger is then free to rotate under the force applied by the threaded rod 551. The keyed aperture may be in a handle portion 562 that is fixed in relation to the barrel of the syringe.

As shown better in FIGS. 6*a-d*, the cross sectional shape of the syringe plunger 516 is configured to rotationally couple the syringe plunger 516 to the linkage 508. The linkage 508 is rotatable with respect to the sheath 500 and the safety plunger 550. Further, the linkage 508 is configured to be rotatable relative to the barrel of the syringe. As the safety plunger 550 exerts a rotational force on the syringe plunger 516 and the syringe plunger 516 is rotationally coupled to the linkage 508 after decoupling of the safety plunger 550 and the syringe plunger 516 (at the sheath release point), further movement of the safety plunger 550 causes rotation of the syringe plunger 516 and the linkage 508 under the force exerted by the second thread of the threaded rod 551.

Referring to FIGS. 6*a-d*, the operation of the apparatus of FIGS. 5*a* and 5*b* is shown. FIG. 6*a* shows the apparatus before use. The safety plunger 550 is linearly coupled to the syringe plunger 516 such that linear motion of the safety plunger 550 results in linear motion of the syringe plunger 516. The syringe plunger 516 is also rotationally coupled to the linkage 508 such that rotation of the syringe plunger 516 results in rotation of the linkage 508.

In FIG. 6*b*, a force is applied by a user to the head of the safety plunger 550, as shown by arrow 564. The syringe plunger 516 has moved to the sheath release point where it is no longer linearly coupled to the safety plunger 550. This point in the exemplary apparatus is at the end of the inward stroke of the syringe plunger 516, when the syringe plunger 516 has reached the bottom of the barrel. In the exemplary apparatus, the syringe plunger 516 decouples from the safety plunger 550 because the ribs 553*a, b* pass completely through the slots in the lip 509 of the linkage 508 and no longer constrain rotation of the linkage 508. The syringe plunger 516 is still rotationally coupled to the linkage 508.

As shown in FIG. 6*c*, continued movement of the safety plunger 550 in the direction of arrow 585 rotates the syringe plunger 516 due to the interaction between the second thread of the safety plunger 550 and the corresponding features of the syringe plunger 516. Rotation of the syringe plunger 516 causes rotation of the linkage 508, as shown by arrows 586 and 588 respectively. Because the linkage 508 acts as a lead screw, rotation thereof causes extension of the sheath 500 in the direction of arrow 589 due to the interaction between the first thread (on the linkage 508) and the corresponding features of the sheath 500. The first thread, which is on the linkage 508 may be configured to provide a ratioed mechanism for deployment of the sheath 580, but need not be so configured. This may be done by increasing an angle of the first thread such that it is greater than the angle of the second thread, which is on the threaded rod 551 of the safety plunger 550. In this way the magnitude of linear motion of the sheath 500 is greater than the magnitude of the linear motion of the safety plunger 550 after the sheath release point.

FIG. 6*d* shows a fully deployed sheath 500 that is at least partially covering the needle. The continued movement of the safety plunger 550 in the direction of arrow 585 results in the continued rotation of the linkage 508 and the syringe plunger 516, as shown by the arrows 586 and 588 respectively. The rotation of those members results in the continued extension of the sheath 500 in the direction of arrow 589.

The skilled person will be able to envisage other embodiments without departing from the scope of the appended claims.

The invention claimed is:

1. An apparatus for use with a syringe for providing a safety syringe, the apparatus comprising:
 a sheath deployable for at least partially covering a needle of the syringe; and
 a sheath actuator for deploying the sheath by interaction with a sheath deployment mechanism,
 wherein the sheath deployment mechanism comprises a rotatable linkage comprising a first thread configured to translate rotation of the linkage into linear motion of the sheath for deployment thereof,
 wherein the sheath is configured to be stationary in relation to the needle until a syringe plunger reaches a sheath release point on its inward stroke, and
 wherein the sheath actuator is configured for deployment of the sheath on movement of the sheath actuator relative to the syringe plunger after the sheath release point.

2. The apparatus according to claim 1, wherein the sheath actuator is configured to be operated by a continued syringe operation action by a user after the sheath release point.

3. The apparatus according to claim 2, wherein the sheath actuator is configured to move relative to the syringe plunger under a force applied by the user during the continued syringe operation action.

4. The apparatus according to claim 1, wherein movement of the sheath actuator relative to the syringe plunger after the sheath release point causes operation of the sheath deployment mechanism, and wherein there is a continuous relationship between movement of the sheath actuator relative to the syringe plunger after the sheath release point and movement of the sheath.

5. The apparatus according to claim 4, wherein the sheath actuator is slidably mountable to the syringe.

6. The apparatus according to claim 1, wherein the sheath deployment mechanism comprises a pinion for interaction with a first rack on the sheath actuator and a second rack on the sheath.

7. The apparatus according to claim 6, further comprising a mount, fixed in relation to the syringe and on which the pinion is mounted.

8. The apparatus according to claim 1, wherein the sheath actuator is configured to rotate the rotatable linkage on movement of the sheath actuator after the sheath release point.

9. The apparatus according to claim 8, wherein the sheath deployment mechanism comprises a second thread, opposed to the first thread and configured to interact with the sheath actuator for rotation of the rotatable linkage.

10. The apparatus according to claim 9, wherein the second thread is located on the rotatable linkage.

11. The apparatus according to claim 9, wherein the sheath actuator comprises a safety plunger for linear coupling to the syringe plunger and configured to decouple from the syringe plunger at the sheath release point.

12. The apparatus according to claim 11, wherein the sheath deployment mechanism comprises a threaded rod extending from the safety plunger, wherein the second thread is located on the threaded rod and is configured to rotate the rotatable linkage on a continued syringe operation action by the user after the sheath release point.

13. The apparatus according to claim 12, further comprising the syringe plunger, wherein the threaded rod is configured to be received in a corresponding recess of the syringe plunger for rotation thereof, and wherein the syringe plunger is rotationally coupled to the rotatable linkage.

14. The apparatus according to claim 13, further comprising a rotation restrictor configured to prevent rotation of the syringe plunger until after the sheath release point.

15. The apparatus according to claim 14, wherein the rotation restrictor comprises features of one or more legs of the safety plunger configured to interact with corresponding features of the rotatable linkage for preventing rotation thereof.

16. The apparatus according to claim 15, wherein the features of the one or more legs of the safety plunger comprise a rib, and wherein the corresponding feature of the rotatable linkage comprises a slot configured to receive the rib.

17. The apparatus according to claim 14, wherein the rotation restrictor comprises a keyed guide configured to interact with the syringe plunger to prevent rotation thereof.

18. The apparatus according to claim 17, wherein the keyed guide comprises a keyed aperture through which the syringe plunger passes, wherein at least part of the syringe plunger has a cross section configured not to be rotatable within the keyed aperture.

19. The apparatus according to claim 1, wherein the sheath actuator is configured to be fixed in relation to the syringe until the syringe reaches the sheath release point.

20. The apparatus according to claim 19, wherein the sheath actuator comprises a handle portion for receiving a user's index and middle fingers during a syringe operation action.

21. The apparatus according to claim 19, wherein the sheath, sheath deployment mechanism and sheath actuator are connected such that release of the retaining lugs allows movement of the sheath actuator and operation of the sheath deployment mechanism.

22. The apparatus according to claim 1, wherein the sheath comprises retaining lugs for holding the sheath stationary with respect to the needle, and configured to be released when the syringe plunger reaches the sheath release point.

23. The safety syringe comprising an apparatus according to claim 1.

* * * * *